United States Patent
Doerr et al.

(10) Patent No.: US 9,026,219 B2
(45) Date of Patent: May 5, 2015

(54) MODULAR UNIVERSAL PROGRAMMING DEVICE

(75) Inventors: Thomas Doerr, Berlin (DE); Carsten Hennig, Berlin (DE); Joachim Elsner, Berlin (DE); Kai Hensen, Jülich (DE); Torsten Dodt, Berlin (DE)

(73) Assignee: BIOTRONIK CRM Patent AG (CH)

( * ) Notice: Subject to any disclaimer, the term of this patent is extended or adjusted under 35 U.S.C. 154(b) by 95 days.

(21) Appl. No.: 12/612,152

(22) Filed: Nov. 4, 2009

(65) Prior Publication Data
US 2010/0114242 A1 May 6, 2010

(30) Foreign Application Priority Data
Nov. 4, 2008 (DE) .......... 10 2008 043 451

(51) Int. Cl.
*A61N 1/08* (2006.01)
*A61N 1/372* (2006.01)

(52) U.S. Cl.
CPC ......... *A61N 1/37235* (2013.01); *A61N 1/37229* (2013.01)

(58) Field of Classification Search
CPC ............ G06F 19/3418; G06F 19/3406; G06F 19/345; A61B 5/686; A61B 2560/045; A61B 5/00; A61B 5/0002; A61B 5/0022; A61B 5/7465; A61N 1/37282; A61N 1/37252; A61N 1/37211; A61N 1/37247; A61N 1/3787; A61N 1/37235; A61N 1/37288; A61N 1/37264; A61N 1/36128; A61N 1/025; A61N 1/36125; G08C 17/02; H04L 67/12; H04L 2209/88; Y10S 128/903; A61M 2205/3523; A61M 2205/3553; A61M 2205/172; H04Q 9/00
USPC .............. 607/1–2, 59–60, 115–116; 715/700, 715/764; 340/539.12; 128/920, 922–923
See application file for complete search history.

(56) References Cited

U.S. PATENT DOCUMENTS

| 5,800,473 A | 9/1998 | Faisandier |
| 7,209,720 B2 | 4/2007 | Balasubramaniyan et al. |

(Continued)

FOREIGN PATENT DOCUMENTS

WO    WO 2008/042610 A2    4/2008

OTHER PUBLICATIONS

Medtronic, Inc.: "Radio Frequency Considerations for the Use of Wireless Telemetry," May 1, 2006, XP002565287, URL: http://www.medtronic.ch/physician/hf/RadioFreqWirelessTelemetryWhitePaper.pdf, Jan. 23, 2010.

(Continued)

*Primary Examiner* — Deborah Malamud
(74) *Attorney, Agent, or Firm* — Craig A. Fieschko, Esq.; DeWitt Ross & Stevens S.C.

(57) ABSTRACT

A universal programming device for individualized patient medical devices such as implants has an RF transceiver (transmitter/receiver), a control unit, and a man-machine interface (or a connection for a man-machine interface). The RF transceiver is configured to receive and transmit data in the MICS frequency band. The control unit is connected to the transceiver and has preconfigured software interfaces, such that the programming device can be expanded by addition of control software modules. The preconfigured software interfaces define a uniform interface for triggering the transceiver, which the control software modules can access. The man-machine interface, e.g., a keyboard and/or a display (and/or the connection for such a man-machine interface) is connected to the control unit.

20 Claims, 7 Drawing Sheets

(56) References Cited

U.S. PATENT DOCUMENTS

| | | |
|---|---|---|
| 7,239,918 B2 | 7/2007 | Strother et al. |
| 7,260,436 B2 * | 8/2007 | Kilgore et al. .................. 607/60 |
| 2007/0060955 A1 * | 3/2007 | Strother et al. ................... 607/2 |
| 2008/0082144 A1 | 4/2008 | Marcotte et al. |
| 2008/0224852 A1 | 9/2008 | Dicks et al. |

OTHER PUBLICATIONS

Stirbys, Petras: "A Challenge: Development of a Universal Programmer," PACE, Bd. 16, Nr. 4, Apr. 1, 1993, pp. 693-694, XP002565288 DOI: 10.1111/j.1540-8159.1993.tb01644.x.

* cited by examiner

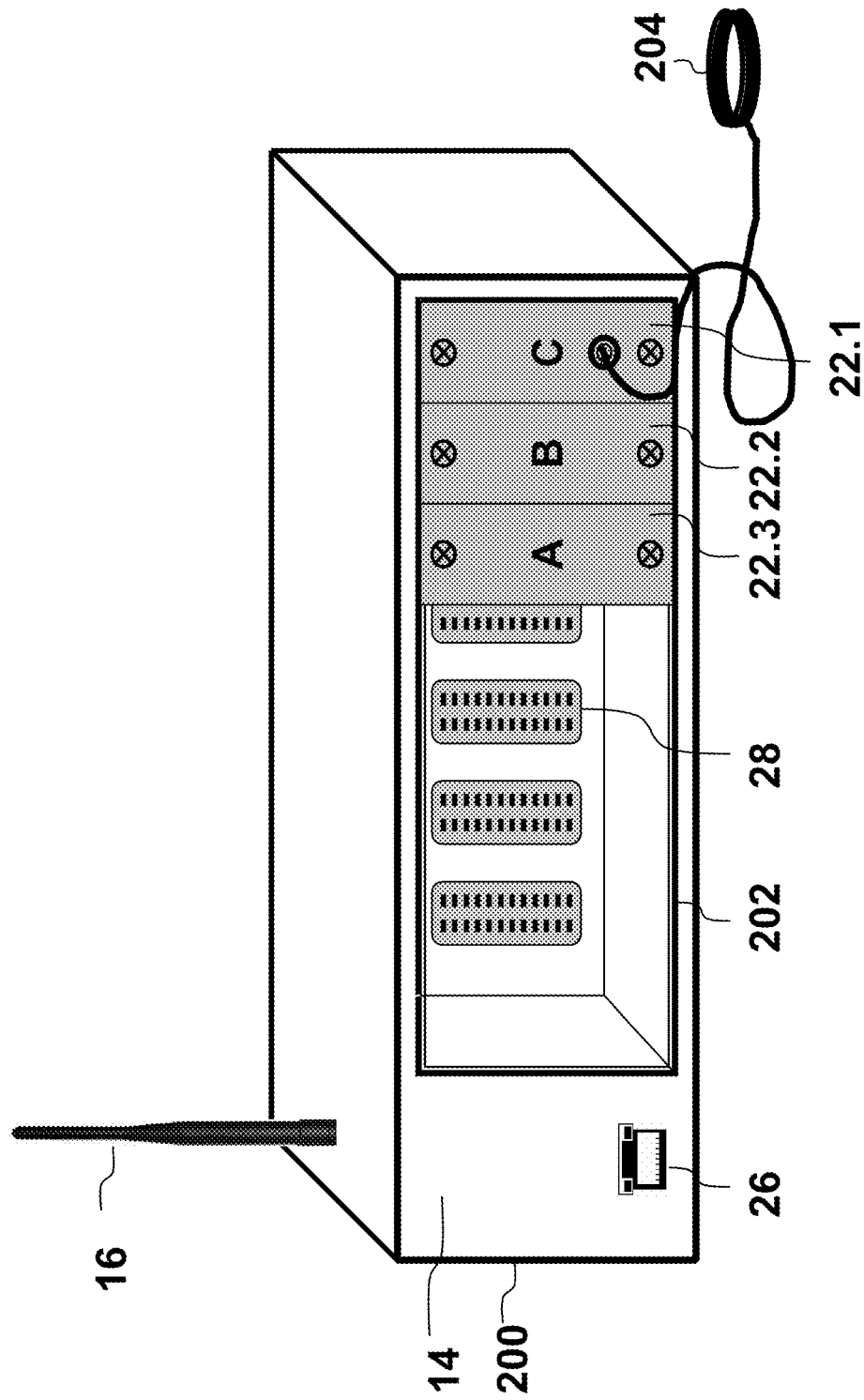

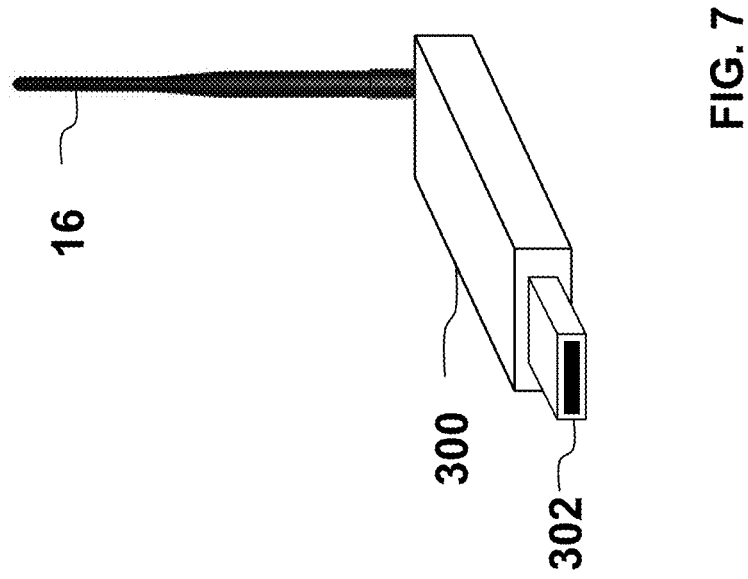

MODULAR UNIVERSAL PROGRAMMING DEVICE

FIELD OF THE INVENTION

The invention relates to a universal programming device for individualized patient medical devices such as implants.

BACKGROUND OF THE INVENTION

U.S. Pat. No. 7,209,790 B2 describes a multi-mode universal programming device which is unfortunately not optimally compatible with devices of other manufacturers. The present invention seeks to create a device with which electronic implants from different manufacturers can be identified, controlled in emergency situations, or completely resupplied with new operating instructions/parameters.

SUMMARY OF THE INVENTION

The invention involves a programming device for individualized patient medical devices such as implants, which has an RF transceiver (radio frequency transmitter/receiver), a control unit, and a man-machine interface (or a connection for a man-machine interface) such as a keyboard and display and/or a touchscreen. The RF transceiver is configured to receive and transmit data in the MICS band (Medical Implant Communication Services band). The control unit is connected to the transceiver and has preconfigured software interfaces, such that the programming device can be expanded with control software modules, with the preconfigured software interfaces defining a uniform interface for triggering the transceiver that can be accessed by the control software modules. The man-machine interface, e.g., a keyboard and/or a display or the connection for a man-machine interface, is connected to the control unit.

The MICS frequency band is provided for medical implant communication services, i.e., data communication with medical implants, and occupies frequencies between 402 and 405 MHz.

The RF transceiver is preferably configured to be suitable for all modulation and protocol methods in the MICS band and to support all manufacturer-specific MIC protocols. The RF transceiver is thus preferably a software-programmable MICS radio.

The control unit preferably has uniform hardware interfaces for manufacturer-specific add-on hardware modules, such that the hardware interfaces are connected to the RF transceiver via the control unit.

The preconfigured software interfaces are preferably configured in such a way that the electronic implants of different manufacturers can at least be identified by adding manufacturer-specific software components.

The programming device preferably has one or more antennas for the MICS communication, these antennas being connected to the RF transceiver.

The add-on hardware modules preferably include driver software for controlling the antennas. The driver software allows implementation of a particular RF protocol.

Each add-on hardware module preferably includes manufacturer-specific software, which includes components for a graphical user interface (GUI) for reproduction via the man-machine interface.

The man-machine interface preferably has at least one display for identification of an electronic implant, which is designed for display of a serial number of an implant or display of a patient's name, for example.

It is likewise preferable for the man-machine interface to have one or more keys that are connected to the control unit for triggering implant-specific emergency functions. For example, an emergency shock can be delivered with such keys in the case of implantable cardioverter/defibrillators (ICDs), or to initiate a safety program in the case of implantable pulse generators (IPGs) such as cardiac pacemakers, or to trigger an "OFF" in the case of medication pumps, so that the programming device can also be utilized for emergency response even without any additional network terminals.

The programming device preferably has additional frequency generators for data communication in frequency ranges other than the MICS frequency range. For example, this allows activation of the MICS communication by prior signaling in frequency bands other than the MICS frequency band. These other frequency bands may be, for example, in the range of 32 kHz to max. 2.5 GHz. This allows data communication in the MICS frequency range to be activated only when it is required for data communication.

The programming device preferably has software frameworks fixedly assigned to it and defined interfaces to control software modules, so that manufacturer-specific control software modules can be embedded in the programming device by means of a software framework such as "COM" or ".net."

The programming device preferably has one or more interfaces to one or more terminals for control of the functions by a user, e.g., a physician. To do so, the programming device is preferably designed so that the terminals can be embedded in the software framework as a "web client." This makes it possible to integrate the programming device into a hospital network and/or the network of a doctor's office, so that it can be used by all computers authenticated in the network.

According to further preferred variants of the invention, the MICS universal programming device is embodied as a USB flash drive and preferably has the dimensions 20×10×30 mm (W×H×D). The MICS universal programming device here is preferably embodied as a USB flash drive, including integrated MICS antennas. The USB flash drive preferably has at least two integrated MICS antennas to allow antenna diversity.

Other advantageous variants of the invention are obtained by combining the preferred features described above.

BRIEF DESCRIPTION OF THE DRAWINGS

The invention will now be explained in greater detail on the basis of exemplary versions depicted in the figures, in which:

FIG. 6: shows the design implementation of such a modular MICS universal programming device; and FIG. 7: shows an alternative implementation of the universal MICS programming device in the form of a USB flash drive.

DETAILED DESCRIPTION OF PREFERRED VERSIONS OF THE INVENTION

Figure 1:
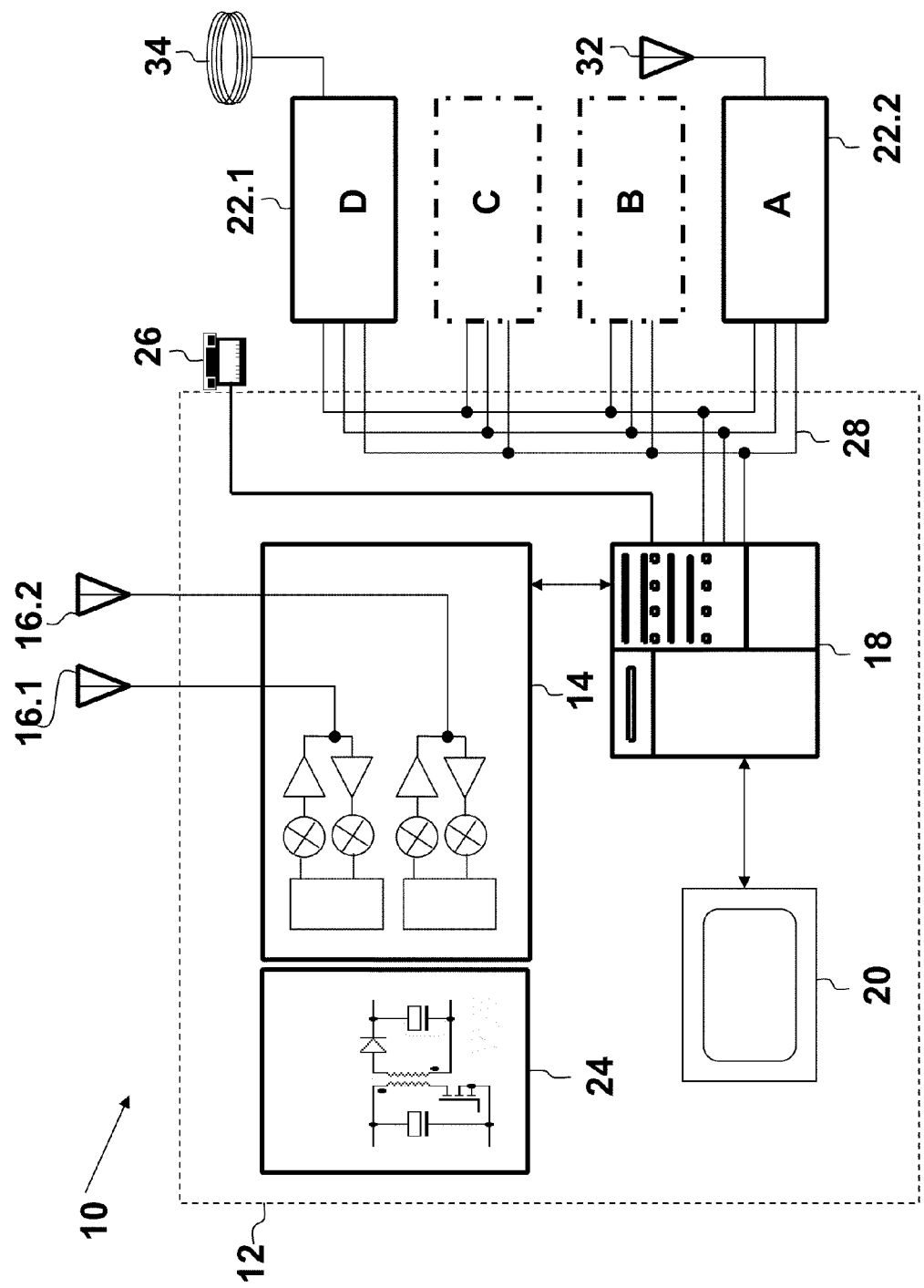
FIG. 1: shows a block diagram of an MICS-band universal programming device.

FIG. 1 shows a block diagram of a MICS-band universal programming device 10. The universal programming device has an MICS base station 12, which includes a dual MICS transceiver 14 with two antennas 16.1 and 16.2. Antenna diversity can be achieved in this way.

A programmable control unit 18 is provided for the control. A touch-sensitive display (touchscreen) 20 is available for operation of the base station 12. A shared power pack 24 is integrated into the base station 12 for supplying electric power to the base station 12 and any add-on hardware modules 22.1 or 22.2. The base station 12 has an Ethernet interface 26 and can be integrated into an existing hospital network or doctor's office network via an Ethernet connection and is preferably controlled from one or more terminals of this network.

Manufacturer-specific add-on hardware modules 22 (22.1, 22.2, etc.) may be integrated into the base station via a defined bus system 28. These add-on hardware modules 22 may include further manufacturer-specific antennas, e.g., for activation of the MICS telemetry, and/or the antennas may be connected to these modules. For example, the module of manufacturer "A" at 22.2 may be connected to a 2.1 GHz antenna 32, and the module of manufacturer "D" at 22.1 may be connected to a coil 34 for inductive communication at 175 kHz.

Figure 2:
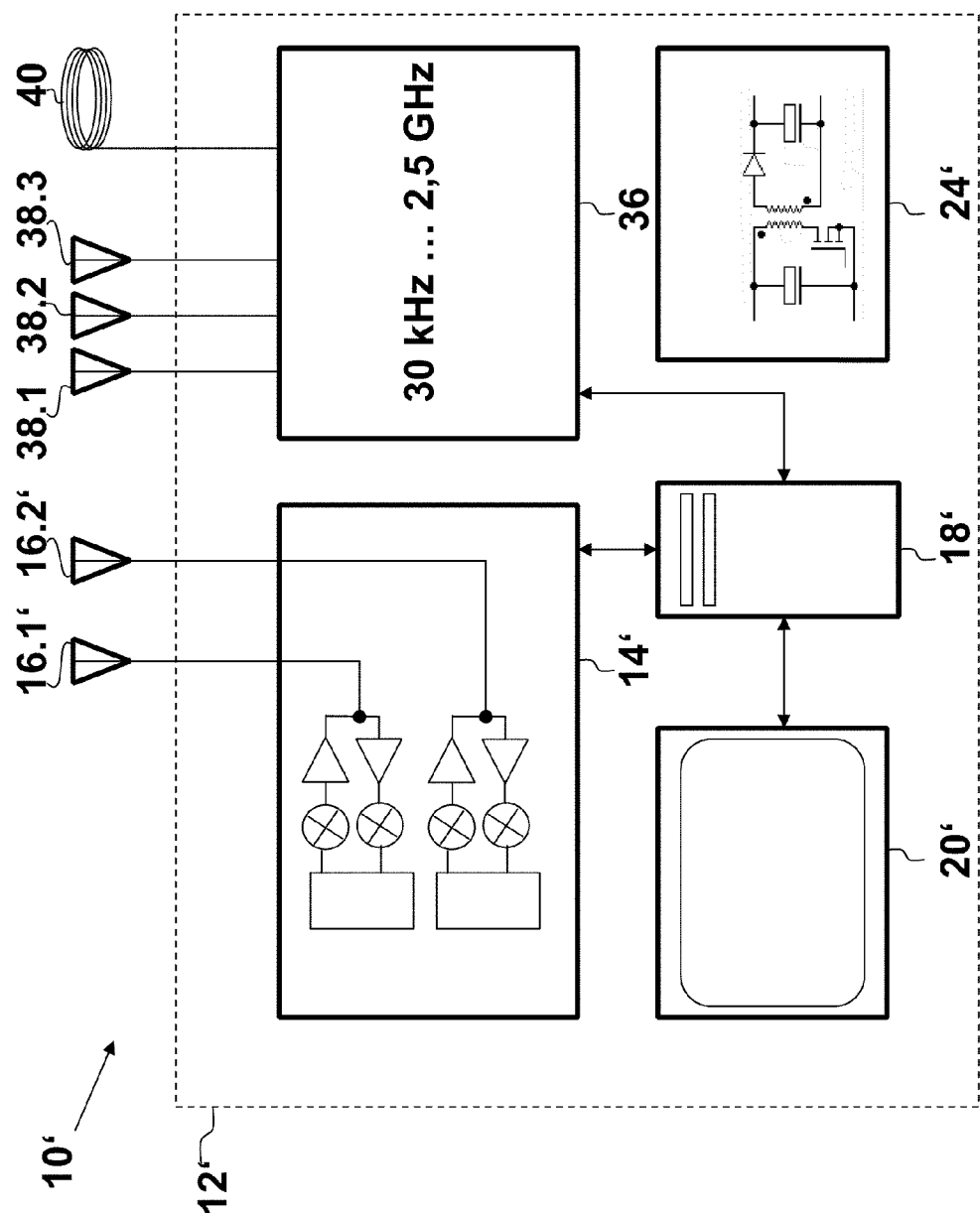
FIG. 2: shows a block diagram of an alternative MICS universal programming device.

FIG. 2 shows a block diagram of an alternative MICS universal programming device 10' having a control unit 18', a man-machine interface (touchscreen 20) connected to the control unit 18', a dual MICS transceiver 14', its MICS antennas 16.1' and 16.2', and a software-programmable radio 36 and its antennas 38.1, 38.2 and 38.3, plus an inductive programming coil 40 and its power supply unit 24'.

The MICS antennas 16.1' and 16.2' are arranged so that antenna diversity can be implemented (antenna diversity being a feature that is known to those skilled in the art).

The software-programmable radio 36 serves to activate the MICS communication in an electronic implant. The software-programmable radio 36 is connected to several antennas 38.1, 38.2 and 38.3 to thereby be able to transmit the frequencies (~30 kHz . . . ~2 GHz) that are used for the activation of the MICS communication. The choice of the antennas that are used is made as a function of the particular frequency sent. The inductive programming coil 40 is selected for the low frequencies.

Figure 3:
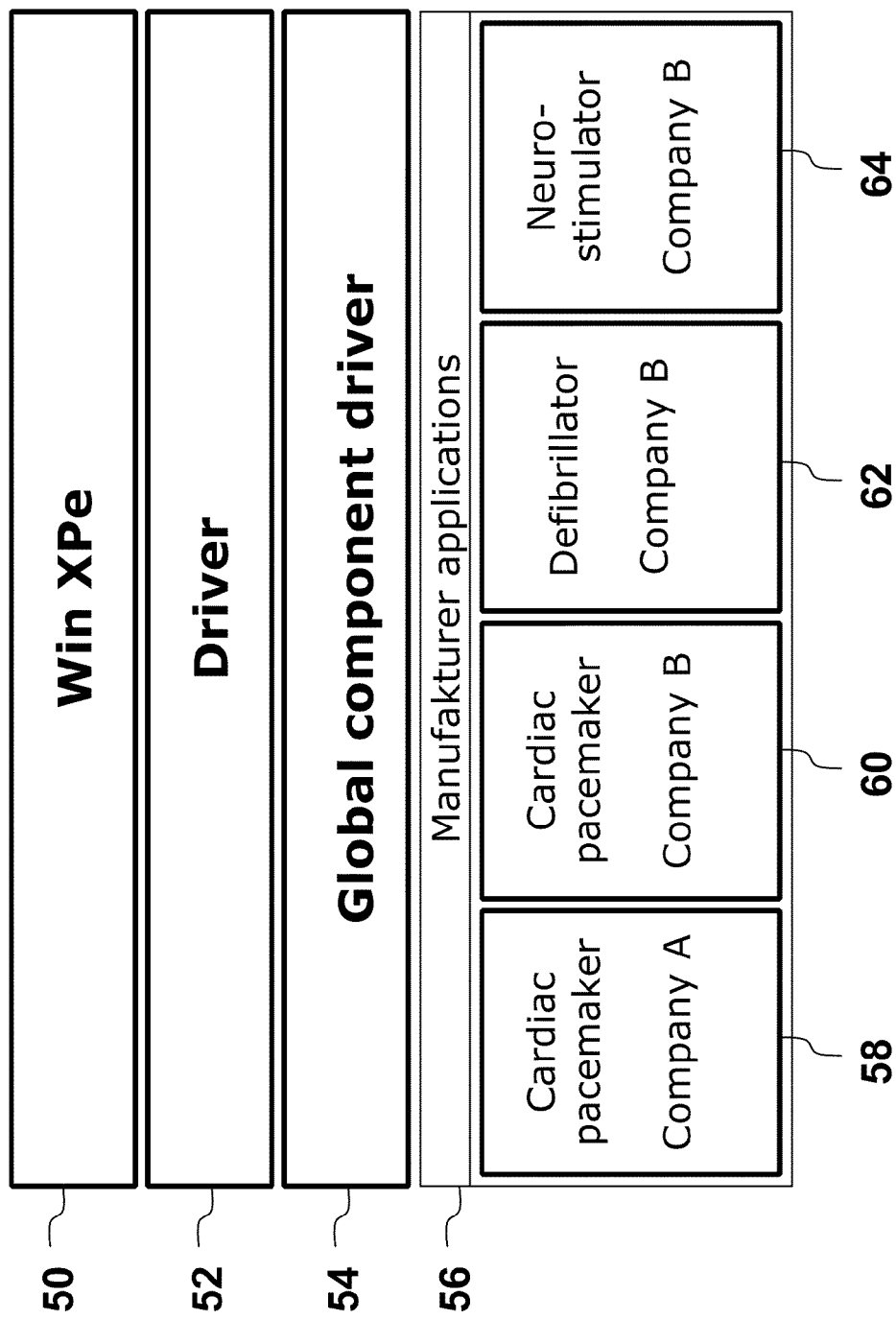
FIG. 3: shows the software architecture of an MICS universal programming device.

FIG. 3 shows the software architecture of such a system. The overall system is based on a Windows XP-embedded operating system 50. For the individual hardware components, specific driver components 52 are available and are then combined into so-called global component drivers 54 and are made available to the manufacturer's applications in the form of software modules 56 via defined preconfigured interfaces. The preferred software technology used here is COM or .net.

The manufacturers then supply implant-specific and manufacturer-specific applications in the form of software modules 56 for the universal programming device 10 or 10'. In the example shown here, two manufacturers are included. Manufacturer A supports a cardiac pacemaker with a corresponding software module 58, while with corresponding software modules 60, 62 and 64, manufacturer B supports a cardiac pacemaker (software module 60), an implantable defibrillator (software module 62) and a neurostimulator (software module 64).

By adding such software modules, the number of supported implants can be expanded indefinitely.

Figure 4:
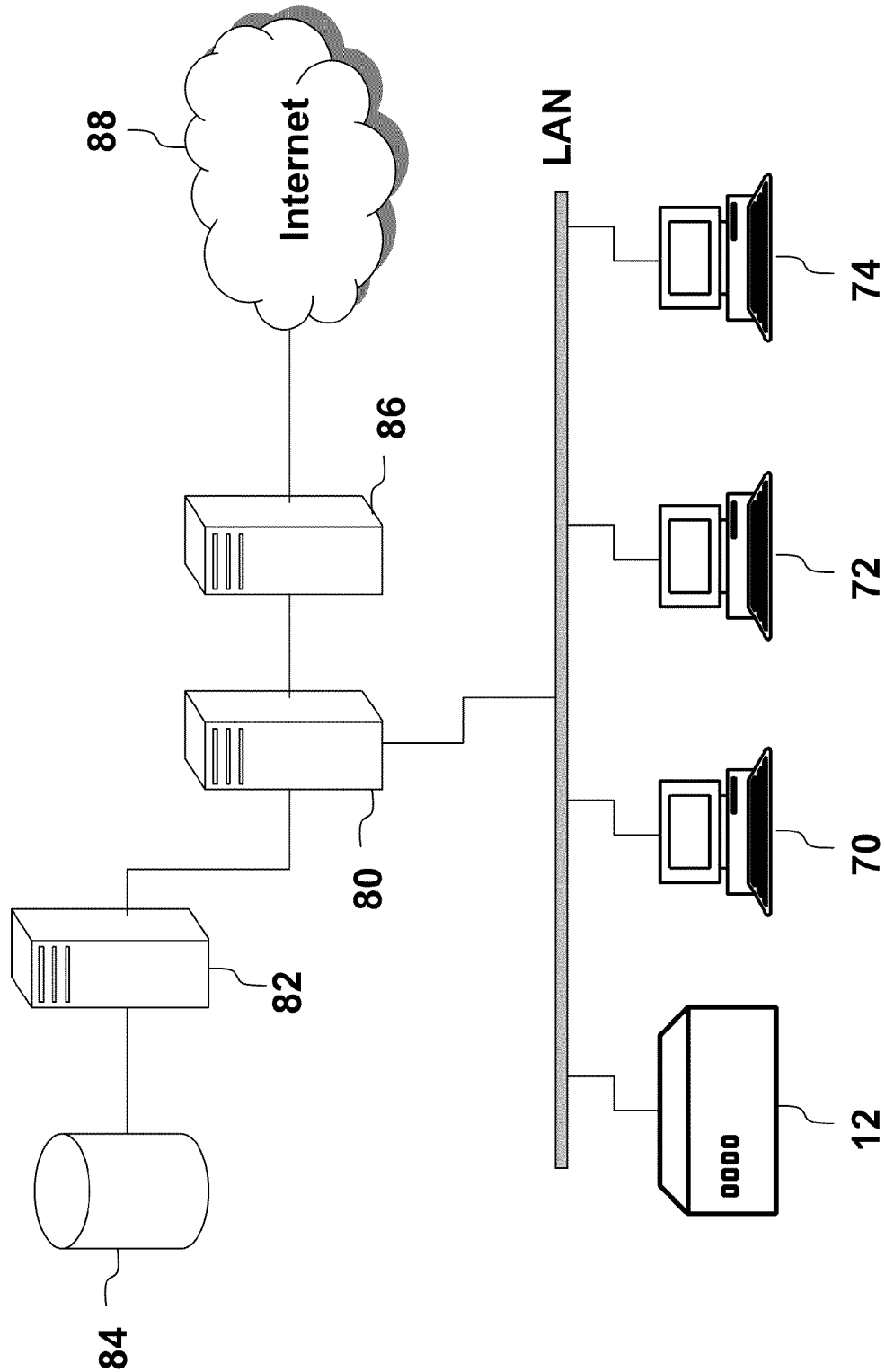
FIG. 4: shows a possible integration of the MICS universal programming device into an existing network.

FIG. 4 shows a possible integration of the MICS universal programming device 12 into an existing network. The MICS universal programming device 12 is connected to the hospital's LAN. The programming device is controlled via workstations 70, 72 and 74 available in the LAN. For example, the system may be configured such that the attending physician and an assistant can be connected to the MICS programming device 12 via two workstations 70 and 72, which are located in the follow-up care room, while in the same session the physician can review and modify the hospital data (e.g., electrocardiograms, therapeutic parameters) of the electronic implant, and the assistant can modify the administrative data (patient data, etc.) of the electronic implant. The workstation 74 in turn has only limited access (e.g., "read only") to the MICS programming device 12 and serves to provide quality control, preparation of doctors' letters and generation of invoices (e.g., DRG coding). This workstation may be accommodated in a different room of the hospital.

The LAN is connected in the traditional manner to a file server 82 via a proxy server 80 and thus allows automatic patient data storage in a database 84 of the hospital information system. An Internet connection 88 is possible via the proxy server 80 and a firewall 86, so that data can also be exchanged via Internet service providers.

Figure 5:
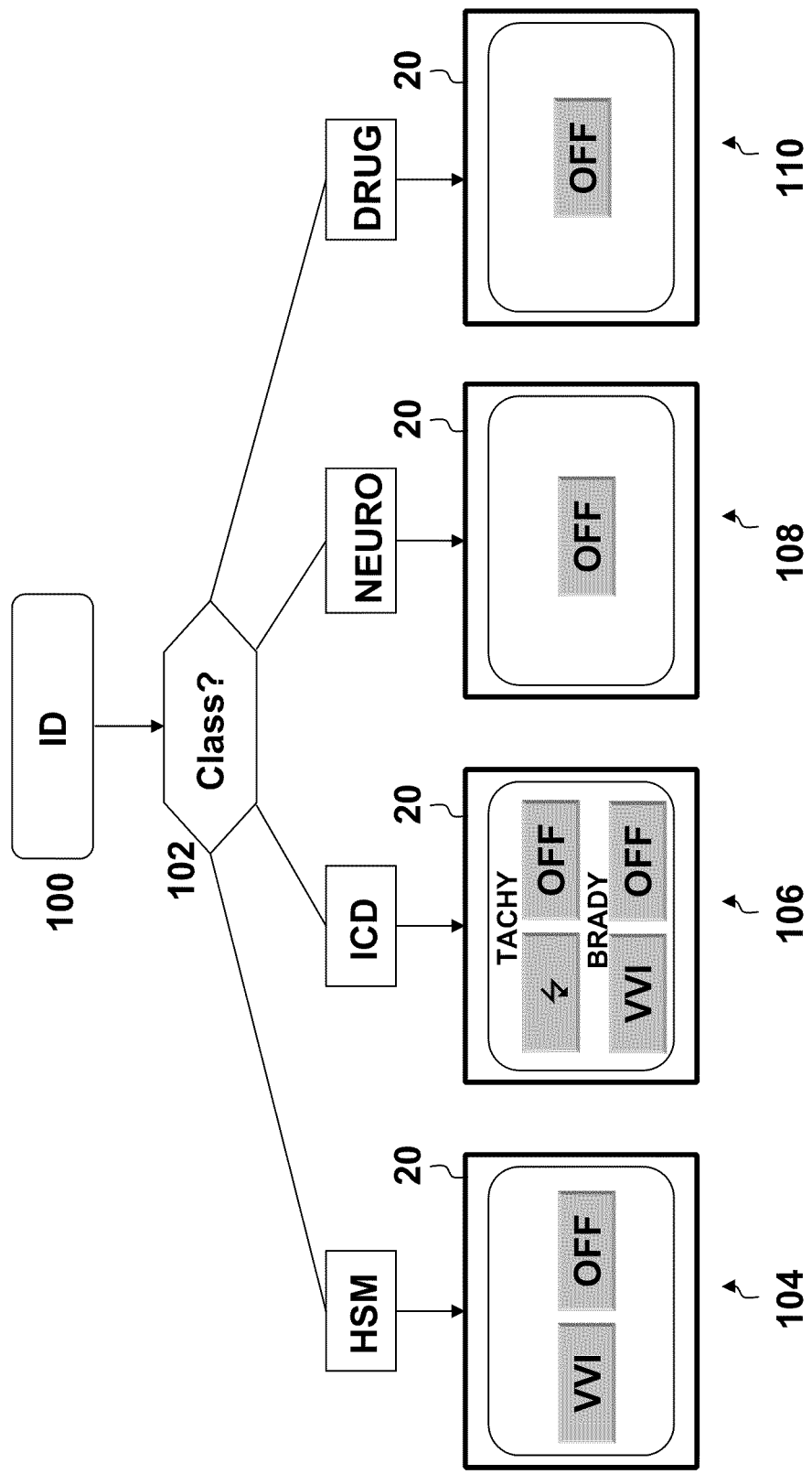
FIG. 5: shows a universal programming device configured as an emergency programming device for use in (for example) an ambulance vehicle or an ambulance aircraft.

FIG. 5 shows a universal programming device 10 or 10' provided in the form of an emergency programming device for use in an ambulance vehicle or ambulance aircraft. This shows the internal logic structure of such a universal programming device. It has a touch screen 20, which offers a graphical user interface (GUI) with diverse displays that change depending on the situation. First there is automatic identification 100 of a particular electronic implant. Then it is assigned 102 to different implant classes. Depending on this assignment 102, various emergency functions are offered on the display 20 of the universal emergency programming device, depending on the implant class. Thus in the case of a cardiac pacemaker, a protective function (VVI) or an OFF mode (OFF) may be programmed by touching the corresponding fields on the touchscreen 20. The corresponding graphical user interface is shown at 104. A graphical user interface for control of a defibrillator is then shown at 106. Here the display functionality also provides an emergency shock (symbolized at the upper left of the display 20 at 106, which when triggered shuts down the antitachycardiac therapy (e.g., with inadequate shock delivery), or which starts a pacemaker protective program or shuts down the pacemaker.

A neurostimulator of an implanted medication pump may be turned off (OFF) in an emergency. Corresponding graphical user interfaces, which are displayed on the touch screen 20 for control of a neurostimulator and/or an implanted medication pump, are shown at 108 and/or 110.

FIG. 6 illustrates the implementation of such a modular MICS universal programming device 10 in a design. The device is formed by a mainframe 200, which includes an MICS transceiver 14 and the respective optimized MICS-band antenna 16. Alternatively, a second MICS transceiver (not shown here) may already be contained in the mainframe and a second antenna may be affixed, so that antenna diversity is possible even with the standard mainframe.

An Ethernet interface 26 is provided to control the universal programming device 10, so that the device can be integrated into any existing hospital or doctor's practice network. In this case, a personal computer (PC), which is present anyway in the hospital and/or doctor's practice, serves as the terminal. The respective graphical user interface (GUI) for display on the screen of the respective personal computer is also supplied, along with the add-on hardware modules 22 from the individual manufacturers via web application.

A slot/socket 202 for assembly with the individual manufacturer's hardware modules is provided in the mainframe 200, with the electric connection being provided by plug strips (bus connectors) 28 on the back of the slot/socket 202. The bus connectors 28 are connected to the bus system shown at 28 in FIG. 1. The figure shows three hardware modules 22 (22.1, 22.2, 22.3) from individual manufacturers A, B and C. The module of manufacturer C also has a connection for an inductive programming coil 204 for activation of the MICS telemetry in the electronic implant.

FIG. 7 shows an alternative implementation of the universal MICS programming device 10 in the form of an MICS USB flash drive 300, which contains a universal MICS-band radio. The MICS antenna 16 or 16' is either integrated into the USB flash drive or is connected externally to the USB flash drive for optimization of the transmission and reception quality.

This MICS-band USB flash drive is controlled via corresponding software components. It is thus possible to implement an extremely inexpensive and universally usable MICS-band universal programmer, which can be connected via a USB plug 302 to each computer having a USB interface.

It will be apparent to those skilled in the art that numerous modifications and variations of the described examples and versions of the invention are possible in light of the foregoing discussion. The disclosed examples and versions are presented for purposes of illustration only, and this patent encompasses all such modifications and alternate versions as may come literally or equivalently within the scope of the claims below.

What is claimed is:

1. A programming device for patient medical implants, the device being configured for installation and/or transport in a medical facility or medical vehicle, the device including:
    a. an RF transceiver configured to receive and transmit data in the MICS frequency band;
    b. MICS communication antennas connected to the RF transceiver;
    c. a control unit:
        (1) connected to the transceiver,
        (2) configured for communication with a man-machine interface,
        (3) including control software modules wherein:
            i. different ones of the control software modules control different types of patient medical implants, the different types including one or more of:
                a) cardioverter/defibrillators,
                b) pacemakers,
                c) neurostimulators, and
                d) medication pumps,
                from one or more different manufacturers; and
            ii. each control software module is configured to control patient medical implants of a specific type,
        (4) including a preconfigured software interface configured to access the control software modules and provide communication between the control software modules and the transceiver;
    d. an external connector configured to physically connect to hardware separate from the programming device and allow data communication therewith.

2. The programming device of claim 1 wherein the RF transceiver is configured to implement different communications protocols, each communications protocol being configured for communication with one or more of the different types of patient medical implants, the different communications protocols being dictated by the control software modules.

3. The programming device of claim 1 wherein the control unit further includes hardware interfaces, each hardware interface being configured to removably connect with a different add-on patient medical implant hardware module, the hardware interfaces being connected to the RF transceiver via the control unit.

4. The programming device of claim 3 further including:
    a. a man-machine interface having at least one display, and
    b. add-on patient medical implant hardware modules, wherein each hardware module includes different software configured to generate a graphical user interface (GUI) on the man-machine interface.

5. The programming device of claim 1 wherein the control software modules are each configured to allow identification of at least one corresponding patient medical implant, with different software modules being configured to identify different types of patient medical implants.

6. The programming device of claim 1 further including a man-machine interface having a display configured to identify a patient medical implant, the display showing at least one of:
    a. a serial number or other identification code identifying the patient medical implant, and
    b. a patient name corresponding to the patient medical implant.

7. The programming device of claim 1 wherein the programming device further includes a frequency generator configured to communicate data in frequency ranges other than the MICS frequency range.

8. The programming device of claim 1 wherein the control unit is configured to provide connections for control of the functions of one or more patient medical implants by a user via one or more man-machine interfaces, the connections being provided as a web client.

9. The programming device of claim 1 wherein the programming device is configured as a USB flash drive.

10. The programming device of claim 9 wherein the USB flash drive has at least one integrated MICS antenna.

11. The programming device of claim 1:
    a. further including a man-machine interface including a display and a data input device,
    b. wherein each of the control software modules of the control unit is configured to:
        (1) adapt the transceiver to communicate with one or more of the different types of patient medical implants, and
        (2) provide a graphical user interface (GUI) on the man-machine interface for entry of control commands to be communicated to the one or more of the different patient medical implants via the transceiver.

12. The programming device of claim 11 further including:
    a. a USB connector, and
    b. a personal computer connected to the USB connector, wherein:
        (1) the man-machine interface is provided in connection with the personal computer, and
        (2) the control unit is connected to the man-machine interface through the personal computer.

13. The programming device of claim 11:
    a. wherein the control unit is configured to
        (1) identify the one of the different patient medical implants to which signals are communicated via the RF transceiver, and
        (2) classify the identified patient medical implant as one of the following implant types:
            (a) a pacemaker,
            (b) a cardioverter/defibrillator,
            (c) a neurostimulator,
            (d) a medication pump, b. further including a preconfigured software interface configured to generate control displays on the man-machine interface, each control display:
   (1) corresponding to one of the different implant types, and
   (2) accepting command inputs configured for the control display's implant type.

14. The programming device of claim 1:
a. further including:
   (1) a man-machine interface including a display and a data input device,
   (2) a transceiver antenna in communication with the RF transceiver,
   (3) hardware interface modules connected to the control unit, each hardware interface module having a module antenna configured for communication with a respective patient medical implant,
b. wherein each control software module is configured to:
   (1) communicate with one of the several different patient medical implants via one or more of the transceiver antenna and the module antennas, and
   (2) provide a graphical user interface (GUI) on the man-machine interface for entry of control commands to be communicated to the one of the several different patient medical implants.

15. The programming device of claim 1:
c. further including add-on patient medical implant hardware modules, wherein each module contains different driver software configured to control the antennas;
d. wherein the control unit further includes hardware interfaces, each hardware interface being configured to removably connect with a different one of the add-on patient medical implant hardware modules, the hardware interfaces being connected to the RF transceiver via the control unit.

16. A programming device for patient medical implants, the device being configured for installation and/or transport in a medical facility or medical vehicle, the device including:
a. an RF transceiver configured to receive and transmit data in the MICS frequency band;
b. MICS communication antennas connected to the RF transceiver;
c. add-on patient medical implant hardware modules, wherein each module contains different driver software configured to control the antennas;
d. a control unit:
   (1) connected to the transceiver,
   (2) configured for communication with a man-machine interface,
   (3) including control software modules wherein:
      i. different ones of the control software modules control different types of patient medical implants, the different types including one or more of:
         a) cardioverter/defibrillators,
         b) pacemakers,
         c) neurostimulators, and
         d) medication pumps,
         from one or more different manufacturers; and
      ii. each control software module is configured to control patient medical implants of a specific type,
   (4) including a preconfigured software interface configured to access the control software modules and provide communication between the control software modules and the transceiver, and
   (5) including hardware interfaces, each hardware interface being configured to removably connect with a different one of the add-on patient medical implant hardware modules, the hardware interfaces being connected to the RF transceiver via the control unit;
d. an external connector configured to physically connect to hardware separate from the programming device and allow data communication therewith.

17. A programming device for patient medical implants, the device being configured for installation and/or transport in a medical facility or medical vehicle, the device including:
a. an RF transceiver configured to receive and transmit data in the MICS frequency band;
b. a control unit:
   (1) connected to the transceiver,
   (2) configured for communication with a man-machine interface,
   (3) including control software modules wherein:
      i. different ones of the control software modules control different types of patient medical implants, the different types including one or more of:
         a) cardioverter/defibrillators,
         b) pacemakers,
         c) neurostimulators, and
         d) medication pumps,
         from one or more different manufacturers; and
      ii. each control software module is configured to control patient medical implants of a specific type,
   (4) including a preconfigured software interface configured to access the control software modules and provide communication between the control software modules and the transceiver;
c. a man-machine interface having one or more keys connected to the control unit configured to trigger emergency functions in a patient medical implant;
d. an external connector configured to physically connect to hardware separate from the programming device and allow data communication therewith.

18. A programming device for patient medical implants, the device being configured for installation and/or transport in a medical facility or medical vehicle, the device including:
a. a man-machine interface including a display and a data input device;
b. an RF transceiver configured to receive and transmit data in the MICS frequency band;
c. a control unit:
   (1) connected to the transceiver,
   (2) configured for communication with a man-machine interface,
   (3) including control software modules wherein:
      i. different ones of the control software modules control different types of patient medical implants, the different types including one or more of:
         a) cardioverter/defibrillators,
         b) pacemakers,
         c) neurostimulators, and
         d) medication pumps,
         from one or more different manufacturers; and
      ii. each control software module is configured to:
         a) control patient medical implants of a specific type,
         b) adapt the transceiver to communicate with one or more of the different types of patient medical implants, and
         c) provide a graphical user interface (GUI) on the man-machine interface for entry of control commands to be communicated to the one or more of the different patient medical implants via the transceiver, (4) including a preconfigured software interface configured to access the control software modules and provide communication between the control software modules and the transceiver;
d. an external connector configured to physically connect to hardware separate from the programming device and allow data communication therewith;
e. one or more medical implant hardware modules, each hardware module:
  (1) having a module antenna configured for communication with one of the different patient medical implants, and
  (2) being connected to the RF transceiver through the control unit.

19. The programming device of claim 18 wherein each of the hardware modules is connected to the programming device by connectors allowing detachable removal and replacement of the hardware module.

20. The programming device of claim 18 wherein each of the hardware modules corresponds to one of the software modules, with each software module connecting its corresponding hardware module to the RF transceiver.

* * * * *